(12) United States Patent
Solar

(10) Patent No.: US 10,398,543 B1
(45) Date of Patent: Sep. 3, 2019

(54) INTRODUCER WITH ROTATABLE RETRACTORS AND OPTIONAL IMPLANT MATERIAL DELIVERY DEVICE

(71) Applicant: Matthew S. Solar, Indialantic, FL (US)

(72) Inventor: Matthew S. Solar, Indialantic, FL (US)

(73) Assignee: Matthew S. Solar, Melbourne, FL (US)

( * ) Notice: Subject to any disclaimer, the term of this patent is extended or adjusted under 35 U.S.C. 154(b) by 43 days.

(21) Appl. No.: 15/681,208

(22) Filed: Aug. 18, 2017

Related U.S. Application Data

(60) Provisional application No. 62/378,097, filed on Aug. 22, 2016.

(51) Int. Cl.

| | |
|---|---|
| *A61B 17/02* | (2006.01) |
| *A61B 17/32* | (2006.01) |
| *A61F 2/12* | (2006.01) |
| *A61B 17/34* | (2006.01) |
| *A61M 5/142* | (2006.01) |
| *A61M 5/315* | (2006.01) |

(52) U.S. Cl.
CPC ............ *A61F 2/12* (2013.01); *A61B 17/0218* (2013.01); *A61B 17/32* (2013.01); *A61B 17/3423* (2013.01); *A61B 17/3468* (2013.01); *A61B 2017/320044* (2013.01); *A61M 5/14228* (2013.01); *A61M 5/14232* (2013.01); *A61M 5/31515* (2013.01)

(58) Field of Classification Search
CPC ....... A61B 17/32; A61B 17/025; A61B 17/02; A61B 17/026; A61B 17/0281; A61B 17/0293; A61B 17/0206; A61B 2017/32004; A61F 2/12
See application file for complete search history.

(56) References Cited

U.S. PATENT DOCUMENTS

| | | | | |
|---|---|---|---|---|
| 5,197,971 A | * | 3/1993 | Bonutti | A61B 17/0218 604/105 |
| 5,345,927 A | * | 9/1994 | Bonutti | A61B 17/0218 600/204 |
| 5,454,365 A | * | 10/1995 | Bonutti | A61B 17/0218 600/204 |
| 5,569,165 A | * | 10/1996 | Chin | A61B 17/0218 294/81.3 |
| 5,722,935 A | * | 3/1998 | Christian | A61B 17/0281 600/204 |
| 5,723,006 A | * | 3/1998 | Ledergerber | A61F 2/12 600/233 |
| 6,096,046 A | * | 8/2000 | Weiss | A61B 17/0206 600/210 |

(Continued)

*Primary Examiner* — Seema Mathew
(74) *Attorney, Agent, or Firm* — Schwegman Lundberg & Woessner, P.A.

(57) ABSTRACT

A device or substance (e.g., a breast implant material) can be introduced through a port placed in a skin incision. A blunt blade can extend laterally with respect to a distal opening of the port. The blade can be rotated with respect to the port beneath a layer of skin, such as to separate the skin from underlying tissue. A device or substance can be introduced through a proximal port opening and then through a distal port opening and into the subject via a channel provided by the port. Rotating the blade can include rotating a first blade with respect to a second blade, such as can be performed by a user with one hand manipulating handles associated with the device.

25 Claims, 12 Drawing Sheets

(56) References Cited

U.S. PATENT DOCUMENTS

| | | | | |
|---|---|---|---|---|
| 6,221,008 B1* | 4/2001 | Keckstein | ......... | A61B 17/0281 |
| | | | | 600/204 |
| 7,762,982 B1* | 7/2010 | Shah | ....................... | A61F 2/12 |
| | | | | 604/96.01 |
| 8,206,443 B2 | 6/2012 | Preissman | | |
| 8,211,173 B2 | 7/2012 | Keller et al. | | |
| 8,550,090 B2 | 10/2013 | Keller et al. | | |
| 8,555,893 B2 | 10/2013 | Keller et al. | | |
| 8,641,758 B1 | 2/2014 | Anderson et al. | | |
| 9,168,126 B2 | 10/2015 | Preissman | | |
| 9,925,028 B1 | 3/2018 | Rosenberg | | |
| 2005/0215851 A1* | 9/2005 | Kim | ..................... | A61B 17/02 |
| | | | | 600/37 |
| 2012/0022575 A1* | 1/2012 | Mire | ................... | A61B 5/4893 |
| | | | | 606/198 |
| 2013/0261402 A1* | 10/2013 | Hawkins | ........... | A61B 17/0293 |
| | | | | 600/214 |
| 2014/0114139 A1* | 4/2014 | Ziolo | .................. | A61B 17/025 |
| | | | | 600/233 |
| 2014/0275801 A1* | 9/2014 | Menchaca | ......... | A61B 17/0218 |
| | | | | 600/212 |
| 2015/0342593 A1* | 12/2015 | Lauchner | .......... | A61B 17/0293 |
| | | | | 600/245 |

\* cited by examiner

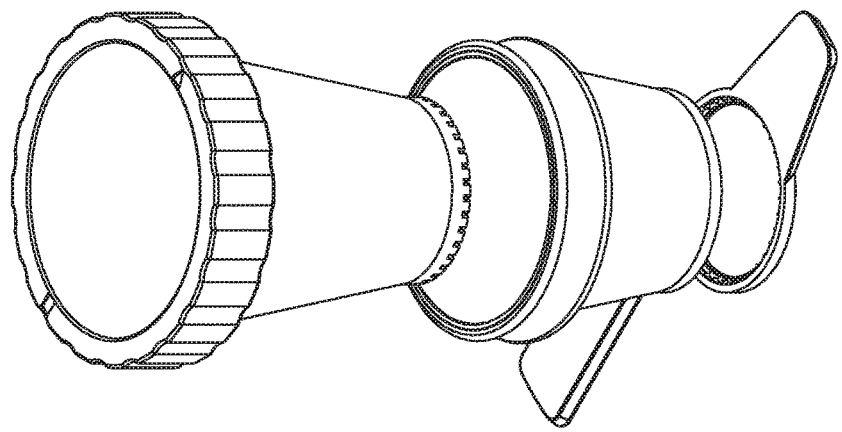
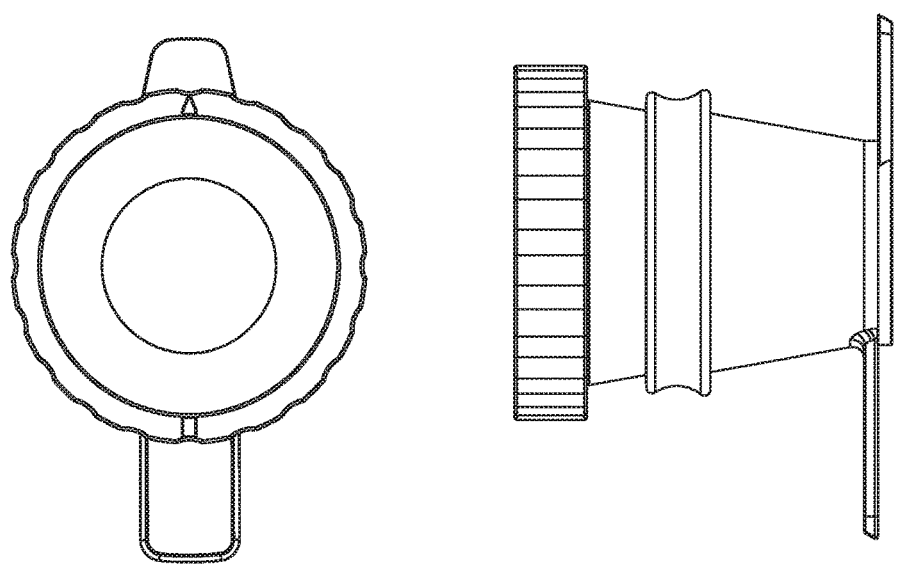
FIG. 3

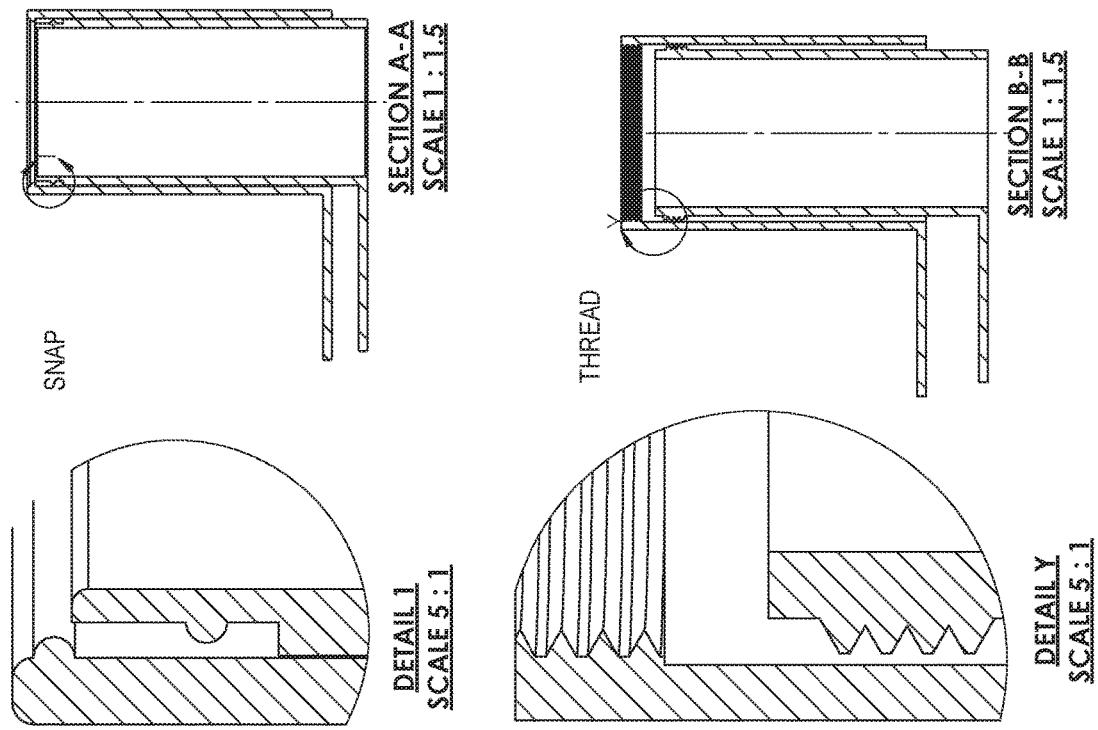
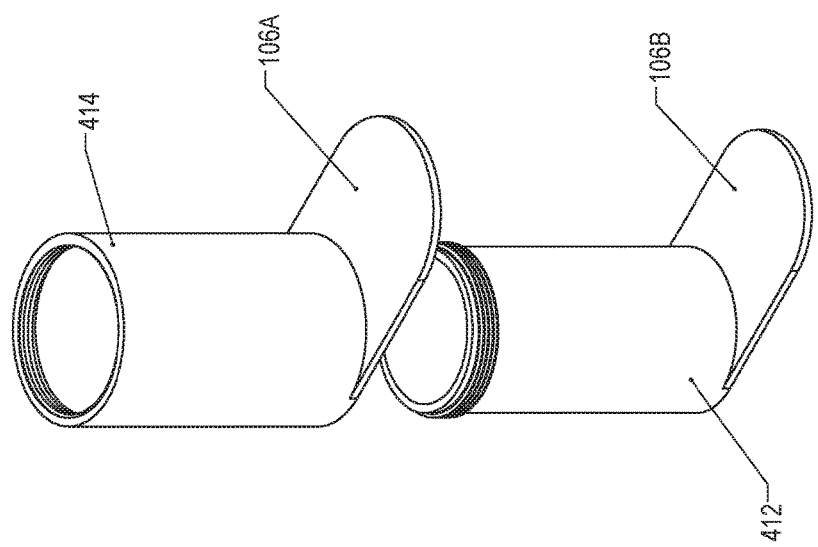
FIG. 5

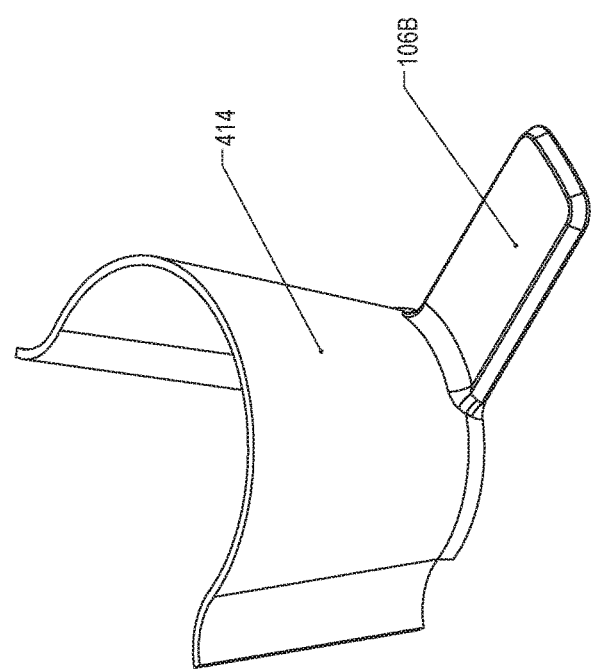
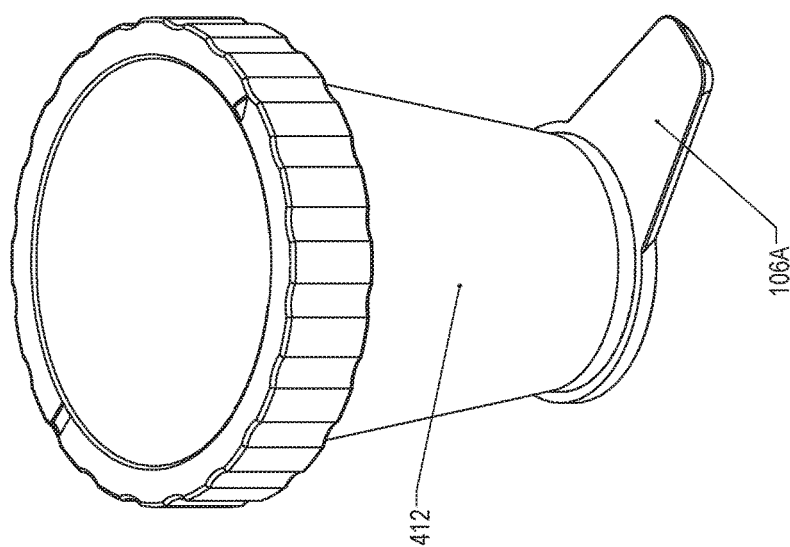
FIG. 7

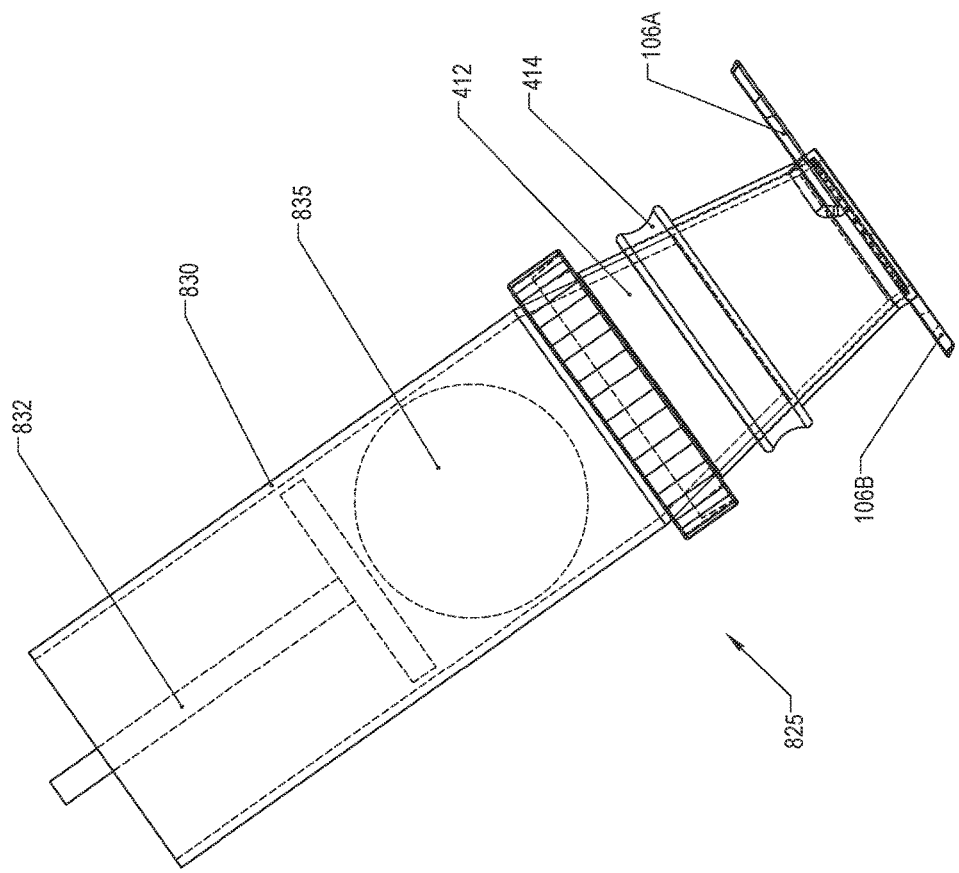
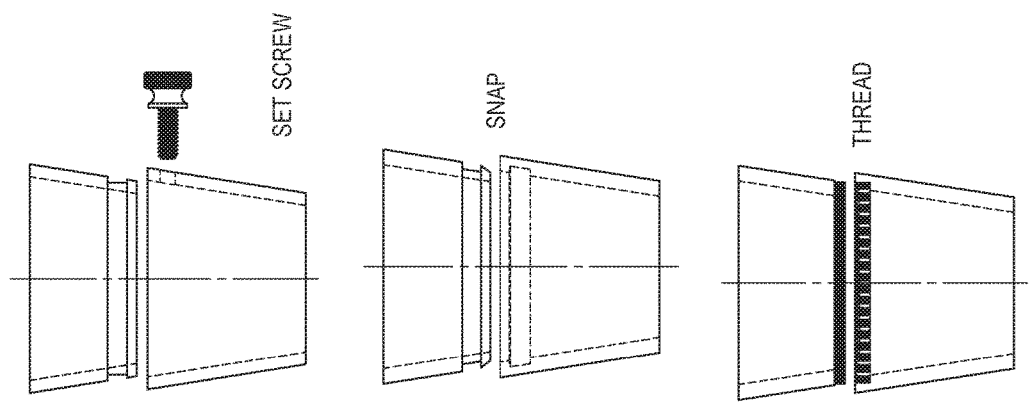
FIG. 8

INTRODUCER WITH ROTATABLE RETRACTORS AND OPTIONAL IMPLANT MATERIAL DELIVERY DEVICE

PRIORITY APPLICATION

This application claims priority to U.S. Provisional Application Ser. No. 62/378,097, filed Aug. 22, 2016, the disclosure of which is incorporated herein in its entirety by reference.

TECHNICAL FIELD

This document pertains generally, but not by way of limitation, to medical devices, and particularly, but not by way of limitation, to an introducer or access port with one or more rotatable retractors.

BACKGROUND

Many types of surgical procedures involve access, such as via an incision, and inserting an instrument or implant into the body via the incision. Sometimes, for such access, it can be desirable to retract the skin around the incision, which may involve pulling skin away from the incision, or away from underlying tissue or organs, such as to allow insertion of the instrument or implant.

For example, a breast prosthesis may involve insertion of a silicone breast implant substance into a subject's breast, such as via an incision. A pair of retractors may be used by the implanting physician to spread the skin around the incision. The retractors may include an elongated handle portion, and an orthogonal blade extending away from the handle portion. The orthogonal blade can be worked under the skin to be retracted, such as to separate the skin to be retracted from underlying tissue or organs to allow easier retraction. The breast implant material can then be inserted through the incision using a desired instrument.

Some illustrative examples of breast implant techniques are mentioned in U.S. Pat. Nos. 8,211,173, 8,641,758, 8,555,893, and U.S. Pat. No. 9,168,126.

SUMMARY

The present inventor has recognized, among other things, that using a pair of retractors for a breast implant or other medical procedure may be cumbersome in that it may require two personnel to perform the procedure: a first person to hold, guide, and manipulate the pair of retractors, and a second person to dispense the implant material or to introduce one or more instruments through the incision. Accordingly, the present inventor has recognized that improved devices and methods of accessing an implant site and retracting tissue around an incision may be desirable.

This document describes, among other things, a pair of retractors that can be mechanically coupled together, and that can be coupled to an introducer, such as to help enable a single person to manipulate the retractors as well as to dispense the implant material or to introduce one or more instruments through the incision. A distal portion of the introducer can be introduced into an incision, such as to provide an "incision ring" or "access port" that can maintain an opening or port by itself, thereby helping avoid any need to pull individual retractors apart. The integrated device, including both introducer and retractors, can provide rotatable retractors.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 shows an example the medical device in which one or more of the handles on the port or the handles on the sleeve can be omitted.

FIG. 5 shows examples in which the sleeve/port and the ring/sleeve can form nested hollow partial or complete cylinders and can each include opposing mating threads, such as to allow rotatable threaded engagement between the sleeve/port and the ring/sleeve.

FIG. 7 shows an example in which the sleeve/port need not include a complete hollow cylindrical sleeve.

FIG. 8 shows examples of one or more techniques for optionally helping attach one or more delivery devices or one or more other medical instruments to the medical device.

DETAILED DESCRIPTION

Figure 1:
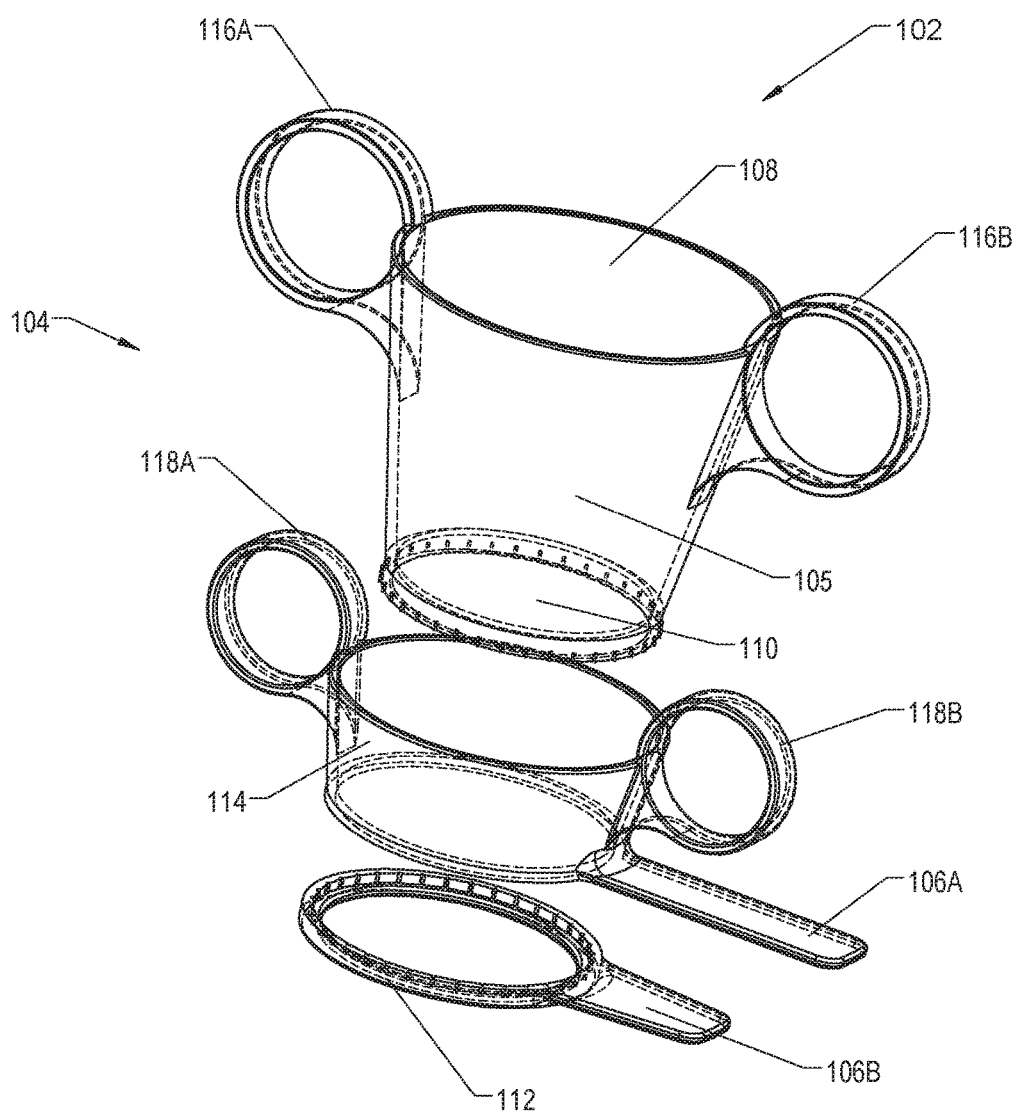
FIG. 1 shows an exploded view example of a surgical access or other medical device.

FIG. 1 shows an exploded view example of a surgical access or other medical device 102, such as can include an introducer 104 with somewhat blunt retractor blades 106A-B such as can be rotatable with respect to each other. The retractor blades 106 can extend orthogonally or otherwise from the introducer 104, such that when the retractor blades 106 are rotated with respect to each other, overlying skin can be separated from underlying tissue or organs. In this example, the introducer 104 can include a cylindrically-walled or other port 105, such as can define a proximal access opening 108 and a distal access opening 110. A retractor blade 106B can be attached to the port 105, such as at or near the distal access opening 110. Such attachment can be via an attachment ring 112, which can be shaped to match the shape of the port 105 at its distal access opening 110. The attachment can include snap-fitting, threading, adhesive or other bonding, or other technique or combination of techniques. After such attachment, the position of the retractor blade 106B can be fixed with respect to the port 105.

Before such attachment, however, a retractor blade 106A can be rotatably coupled to the port 105, such as via a ring or sleeve 114 that can be slipped over an outer surface of the port 105 such as to allow rotation of the retractor blade 106A with respect to the port 105. The attachment of the retractor blade 106B, such as via its attachment ring 112, can be used to capture the sleeve 114 against the port 105 while still allowing rotation of the sleeve 114 about the port 105. This can allow the retractor blades 106A and 106B to be rotated with respect to each other, such as around a full 360 degree perimeter of the port 105 or a desired portion of such perimeter.

The cylindrical or other wall of the port 105 can be tapered, such as from a wider proximal access opening 108 inward toward a narrower distal access opening 110. The sleeve 114, attached to the retractor blade 106A, can include a similar taper to that of the cylindrical wall of the port 105, such as to limit a distance in the proximal direction that the sleeve 114 can travel when the sleeve 114 is placed about the port 105 for being captured between the port 105 and the ring 112 or other feature attached to the retractor blade 106B, while still allowing rotation of the sleeve 114 with respect to the port 105. Additionally or alternatively, a circumferential ridge or protrusion or other feature about the outer surface of the cylindrical wall of the port 105 can be included such as to limit travel of the sleeve 114 in the proximal direction when it is positioned or located about the port 105. Such a circumferential ridge or protrusion or other feature about the outer surface of the sleeve 114 can additionally or alternatively be used to snap fit into, or otherwise engage or fit into, a corresponding circumferential recess about an inner surface of the sleeve 114, such as to provide a circumferential guide upon and about which the sleeve 114 can rotate.

The port 105 can include one or more handles 116 or other features, for example, such as a pair of laterally protruding rings or other handles 116A-B that can be located on or formed together with or attached to opposing sides of the port 105, such as at or near the proximal opening 108. The sleeve 114 can include one or more handles 118 or other features, for example, such as a pair of laterally protruding rings or other handles 118 that can be located on or formed together with or attached to opposing sides of the sleeve 114, such as at positions that can be aligned with those of the one or more handles 116 attached to the port 105. In this way, a physician or other user can grasp the one or more handles 118, the one or more handles 116, or both, such as for rotating the handles 118 with respect to the handles 116, thereby rotating the retractor blade 106A with respect to the retractor blade 106B, such as to help separate skin around an incision from underlying tissue or organ.

In an example, when the handles 116 are aligned to corresponding handles 118, the retractor blades 106A-B are also circumferentially aligned. In this position, it can be easier to insert the aligned retractor blades 106A-B into a desired surgical incision, and work the distal portions of the port 105 and the sleeve 114 into the incision, before then rotating the retractor blades 106A-B with respect to each, such as to help pull skin away from the incision or away from underlying tissue or organs.

Figure 2:
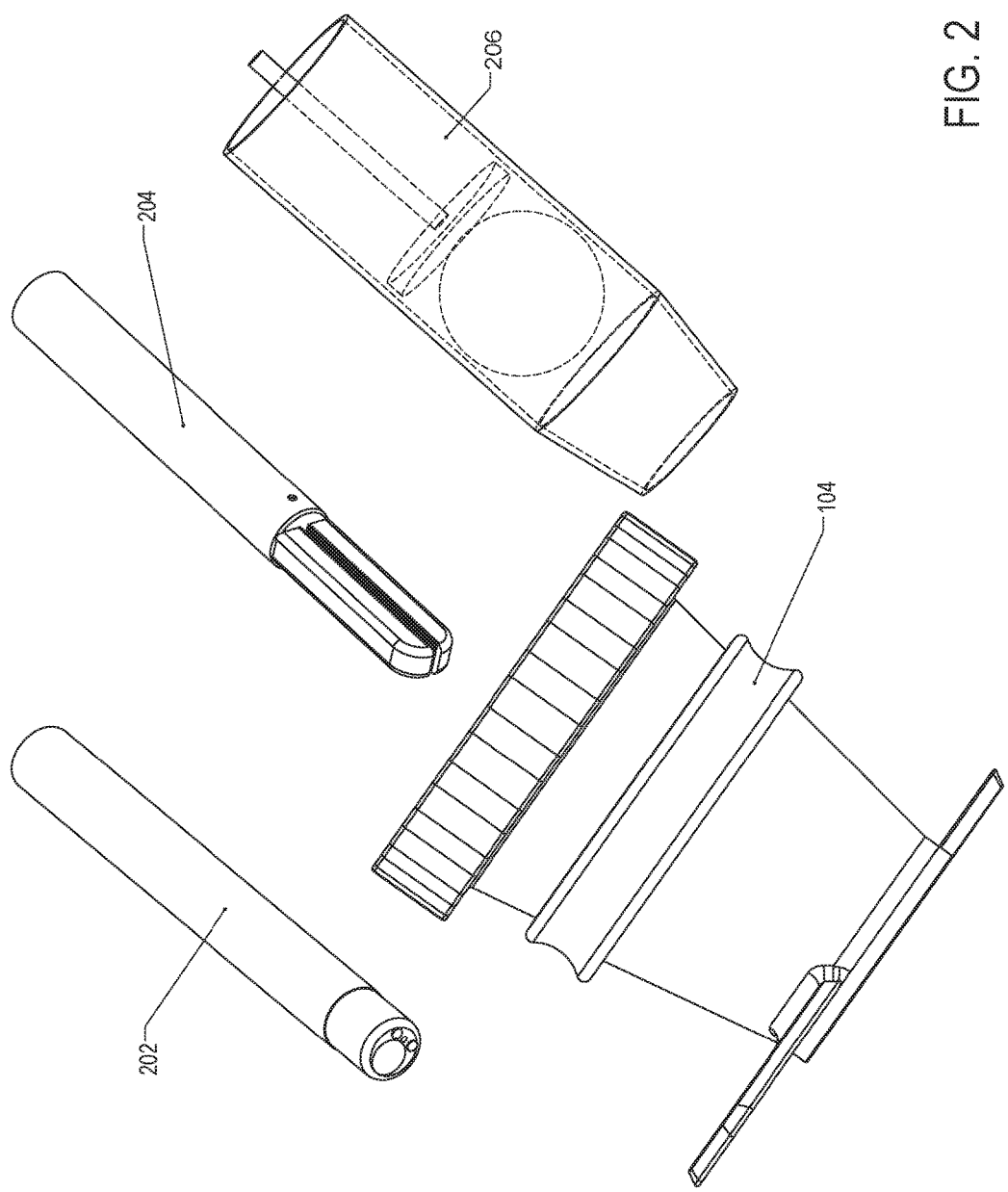
FIG. 2 shows an example of the introducer such as can be used with one or more other medical instruments, such as can be introduced into an incision or other opening in a subject via the introducer.

FIG. 2 shows an example of the introducer 104 such as can be used with one or more other medical instruments, such as can be introduced into an incision or other opening in a subject via the introducer 104. For example, the introducer 104 can be used with one or more of: a visualization instrument 202, such as a camera, a light, a laparoscope, an ultrasound or optical or other local imaging device or the like; a surgical tool 204 such as a trocar, a biopsy needle or other needle, or a forceps or the like; or a substance delivery device 206 such as a catheter, a funnel, a syringe or the like. For example, a visualization instrument 202 such as a camera can be inserted into the introducer 104, such as via its proximal access opening 108. One or more surgical tools or substance delivery devices can be inserted into the subject via the introducer 104 a similar manner.

One or more LEDs or other lights can be included and located at a distal portion of the introducer 104, such as for providing lighting to enable a user or instrument to better view a region within the incision. A battery or other power source can be included with the introducer 104 and electrically coupled to the lights. Additionally or alternatively, a seal or valve (e.g., a tricuspid valve) can be located within a proximal or distal portion of the introducer 104, such as to inhibit fluid passage through the seal or valve in its closed state. This can be useful, for example, in an orthopedic procedure, where there may be liquid within the incision that is desired to be retained within the incision.

FIG. 3 shows an example the medical device 102 in which one or more of the handles 116A-B on the port 105 or the handles 118A-B on the sleeve 114 can be omitted. To help a physician or other user to better grip one or more portions of the medical device 102, one or more portions of an outer circumferential surface of one or both of the port 105 or the sleeve 114 can include a ridged, knurled, or other suitably textured outer circumferential surface, such as can be formed while molding, milling, or otherwise processing one or more such components. The sleeve 114 can have a smooth inner circumferential surface, such as to help aid in the insertion of a distal portion of the port 105 within the sleeve 114, or to help the sleeve 114 freely rotate about a distal portion of the port 105. For example, a proximal circumferential outer surface of the port 105 can be knurled or textured to assist user gripping, while a distal circumferential outer surface of the port 105 can be smooth to assist free rotation of the sleeve 114 about the port 105. Additionally or alternatively, the circumferential outer surface of one or both of the port 105 or the sleeve 114 can be inwardly curved, such as to provide a degree of concavity that can additionally or alternatively help the physician or other user in gripping or grasping one or both of these components.

Figure 4:
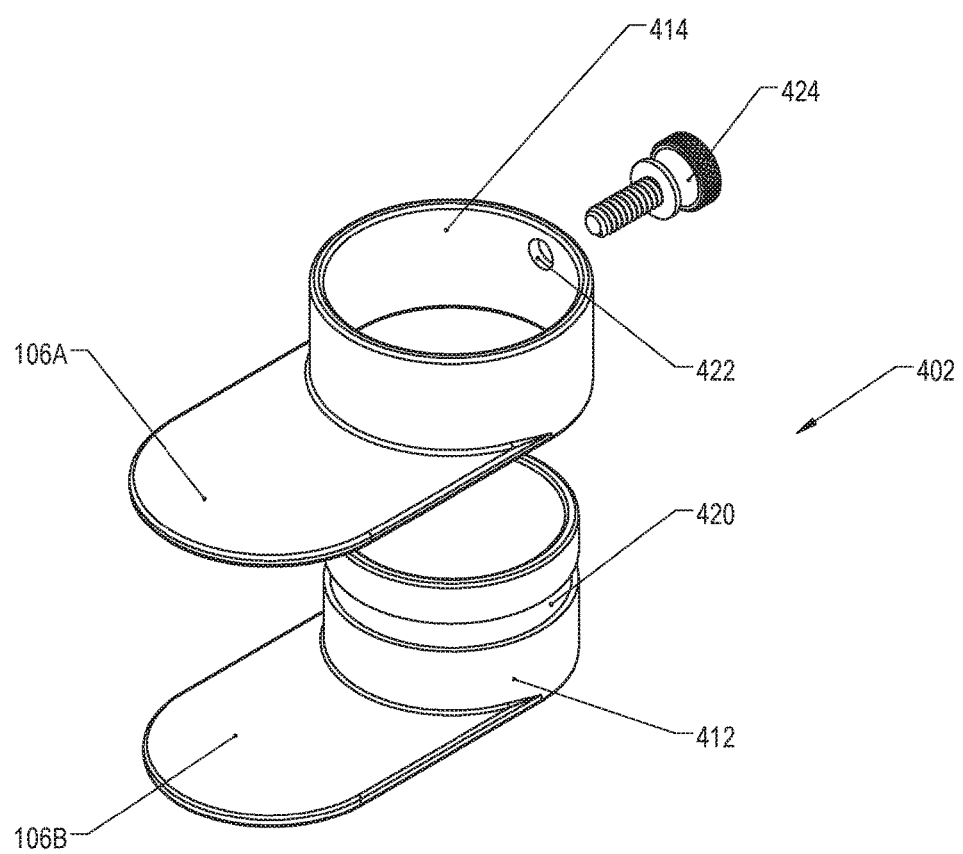
FIG. 4 shows an example of a low profile medical device version of the medical device.

FIG. 4 shows an example of a low profile medical device 402 version of the medical device 102. In the low profile medical device 402, the port 105 can be combined with the sleeve 114, such as to provide an integrated sleeve/port 414 that can be seated on, coupled to, and rotatable with respect to a ring/sleeve 412 from which the retractor 106B can laterally extend. The sleeve/port 414 can include the other retractor 106A extending laterally, such that the retractors 106A-B can be rotated with respect to each other when the sleeve/port 414 is rotated with respect to the ring/sleeve 412.

The retractors 106A-B can be molded or otherwise integrally formed with the respective one of the sleeve/port 414 or the ring/sleeve 412, or can be attached thereto, such as using one or more of a variety of methods, such as can include one or more of gluing, welding, molding, or otherwise forming or attaching one or more such components.

The ring/sleeve 412 can include an outer circumferential groove 420. The sleeve/port 414 can include an opening 422 through which a pin or screw 424 can be passed when the sleeve/port 414 is snapped onto or otherwise placed upon the ring/sleeve 412. The pin or screw 424 can ride within the groove 420, such as to help maintain the coupling between the sleeve/port 414 and the ring/sleeve 412, while still permitting the sleeve/port 414 to rotate with respect to the ring/sleeve 412, such that the retractors 106A-B can rotate with respect to each other. Openings in the sleeve/port 414 and the ring/sleeve 412 can be aligned with each other, such as to permit one or more instruments or other objects to be passed through the sleeve/port 414 and the ring/sleeve 412 into the incision in the subject. The groove 420 can instead be included on the sleeve/port 414 and the ring/sleeve 412 can instead include the opening 422 through which the screw 424 can be passed. Other engagement features can similarly be exchanged between the sleeve/port 414 and the ring/sleeve 412. The device 402 can also be flipped upside down, such that the sleeve/port 414 is closer the incision in the patient than the ring/sleeve 412.

FIG. 5 shows examples in which the sleeve/port 414 and the ring/sleeve 412 can form nested hollow partial or complete cylinders and can each include opposing mating threads, such as to allow rotatable threaded engagement between the sleeve/port 414 and the ring/sleeve 412. Additionally or alternatively, one or more snap-fit coupling features can be included on respective the sleeve/port 414 and the ring/sleeve 412, such as to allow these components to be rotatably engaged with each other, such as to allow the retractors 106A-B to rotate with respect to each other.

Figure 6:
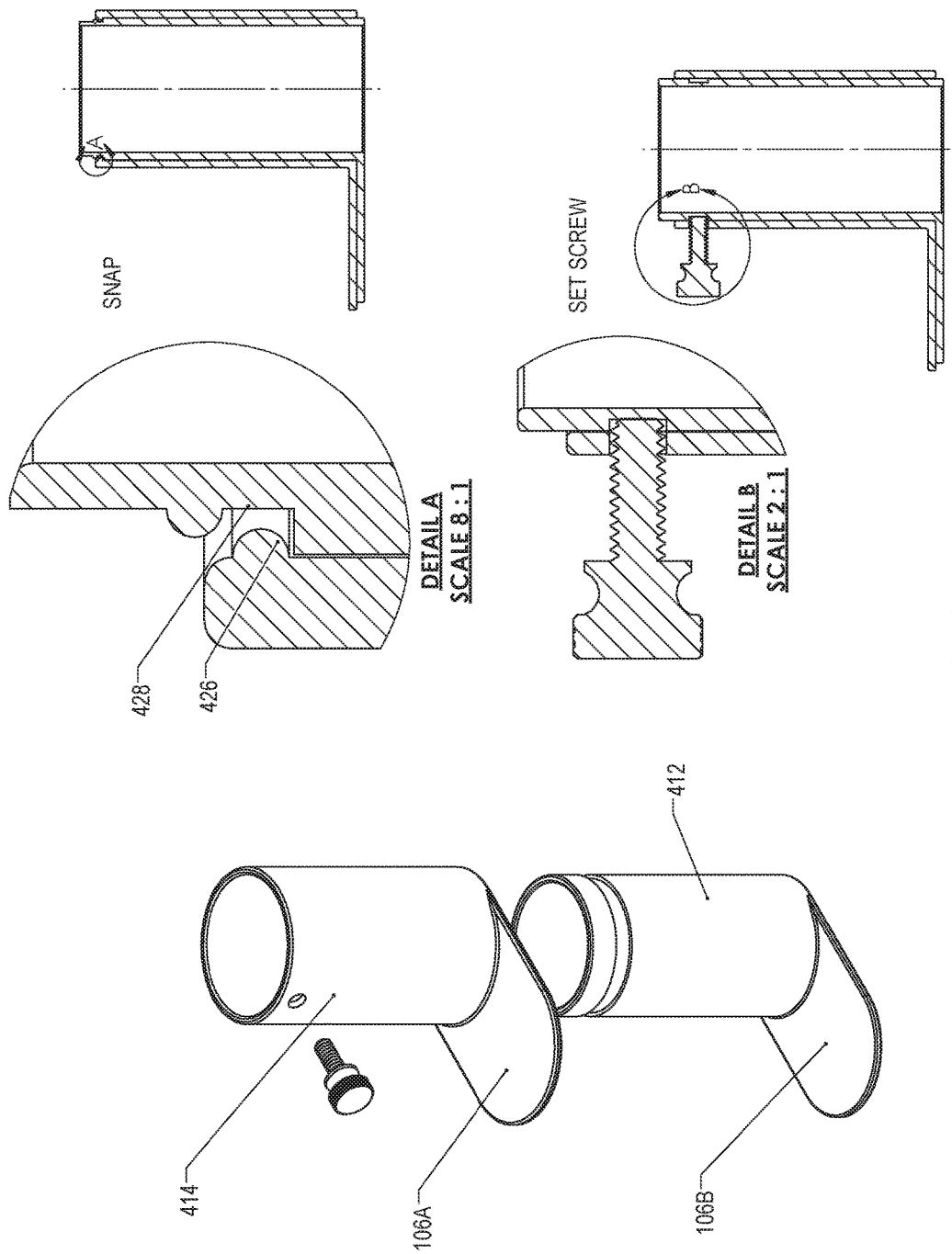
FIG. 6 shows various examples of coupling the nested hollow partial or complete cylinders of the sleeve/port and the ring/sleeve, such as to allow the retractors to rotate with respect to each other.

FIG. 6 shows various examples of coupling the nested hollow partial or complete cylinders of the sleeve/port 414 and the ring/sleeve 412, such as to allow the retractors 106A-B to rotate with respect to each other. For example, the sleeve/port 414 can include one or more male or female engagement features, such as a partial or complete circumferential ridge or one or more protrusions 426, such as along its inner circumferential surface. Similarly, the ring/sleeve 412 can include one or more corresponding mating female or male engagement features, such as a partial or complete outer circumferential groove or indentations 428 along its outer circumferential surface. In such an example, when the ring/sleeve 412 is inserted into the sleeve/port 414, such as through the proximal opening 120 of sleeve/port 414, these two components can snap together into engagement. Additionally or alternatively, the sleeve/port 414 can include one or more openings 422 through its surface, and ring/sleeve 412 can include one or more grooves, indentations 428 or other engagement features of similar size along its outer circumferential surface. In such an example, when inserted into the sleeve/port 414 through the proximal opening 120 and aligned with one or more openings 422, a screw, bolt, rivet, pin, or other coupling or fastening mechanism 424, or a combination thereof, can be inserted through the one or more holes 422 to engage sleeve/port 414 with the ring/sleeve 412.

One or more portions of the outer circumferential surface of sleeve/port 414 and the inner circumferential surface of ring/sleeve 412 can include one or more grooves, ridges, threads, or suitable textures or a combination thereof such to help engage and allow rotation of the sleeve/port 414 with respect to the ring/sleeve 412.

FIG. 7 shows an example in which the sleeve/port 414 need not include a complete hollow cylindrical sleeve, but can instead include a collar that can deformably laterally or coaxially snap onto and partially encompass or cover the outer circumferential surface of the ring/sleeve 412 (or vice-versa, such as with the ring/sleeve 412 including a collar that can deformably snap onto or into the sleeve/port 414).

FIG. 8 shows examples of one or more techniques for optionally helping attach one or more delivery devices or one or more other medical instruments to the medical device 102, 202. For example, an inner or outer circumferential surface of one or more of the sleeve/port 414 or the ring/sleeve 412 can include one or more of a grooved, ridged, threaded, or other suitably textured surface, or a combination of surfaces, such that the medical instruments can be threaded or otherwise engaged into place. Additionally or alternatively, the sleeve/port 414 can include one or more holes through its surface. In such an example, when the medical instrument has at least one indentation along its outer circumferential surface, when inserted into sleeve/port 414 through the proximal access opening and aligned with the one or more holes, a screw, bolt, or any fastening mechanism can be inserted through one or more holes to fasten the sleeve/port 414 with the medical instrument.

Similarly, the sleeve/port 414 or the ring/sleeve 412 can include one or more protrusions or other male or female engagement features along its inner circumferential surface, such as for mating with and snap-fitting or otherwise engaging a medical instrument thereto, such as an auxiliary material introducer device 825. The material introducer device 825 can include a hollow tubular cylinder, funnel, or other chamber 830, such as with a piston or plunger 832. The plunger 832 can be introduced into and driven coaxially into chamber 830, such as to push a silicone breast implant or other substance or material 835 distally outward from the chamber 830 such as into or beyond the incision into the patient via the sleeve/port or the ring/sleeve 412.

Figure 9:
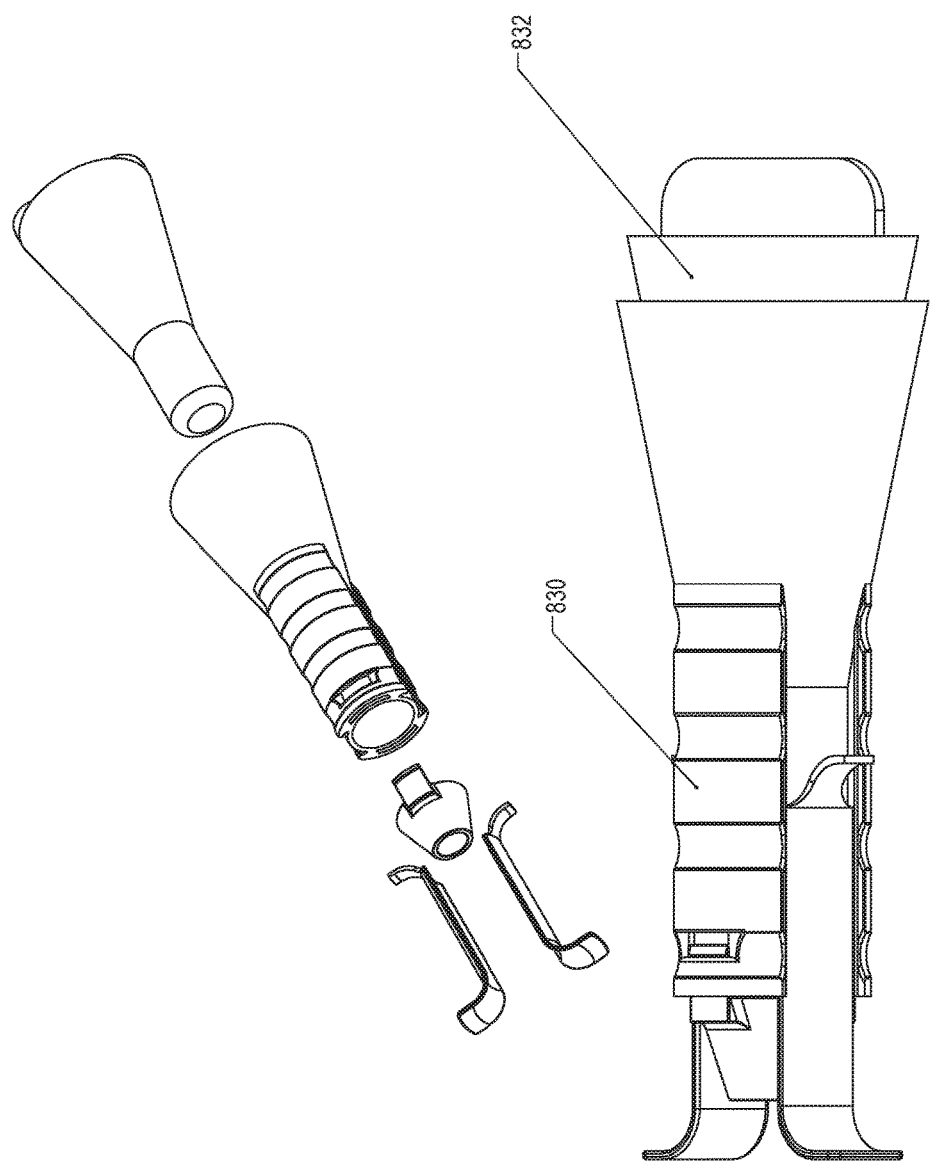
FIG. 9 shows an example of a chamber and plunger, which can be used alone or in combination with another device to help dispense the material.
Figure 10:
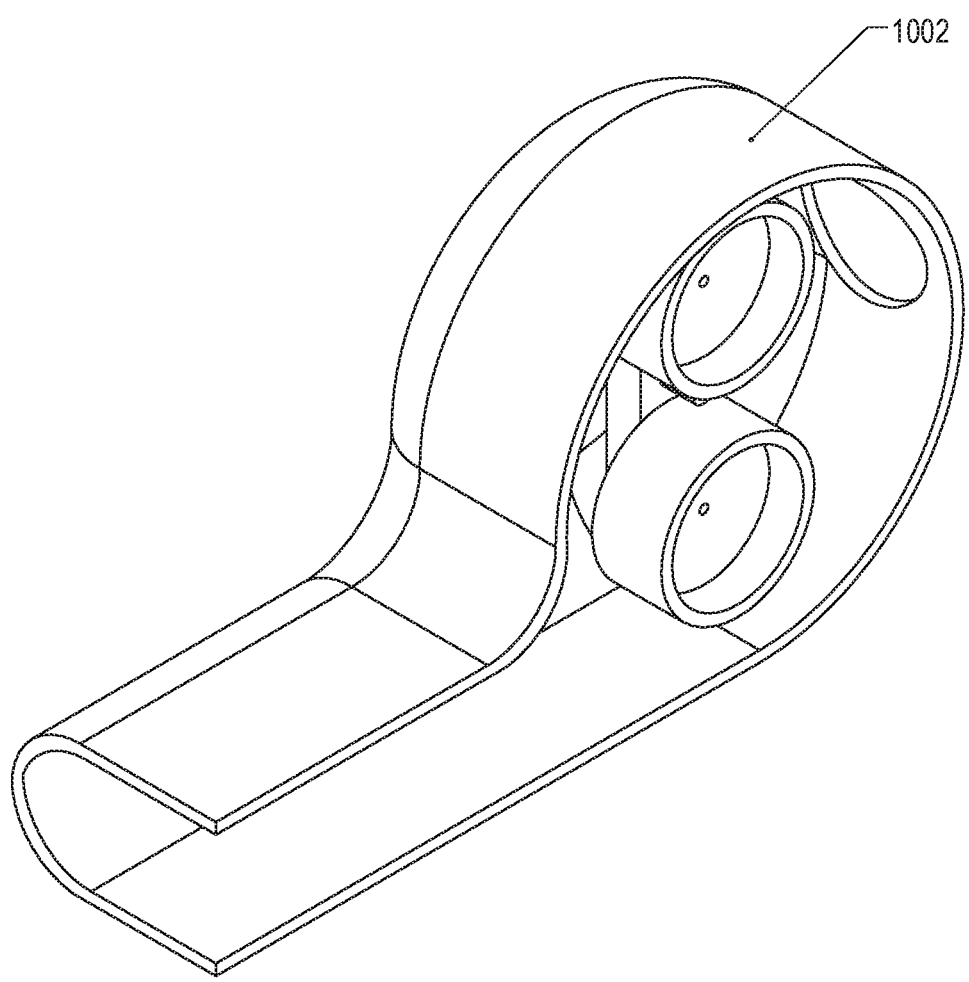
FIG. 10 shows an example of a peristaltic or other pump.
Figure 11:
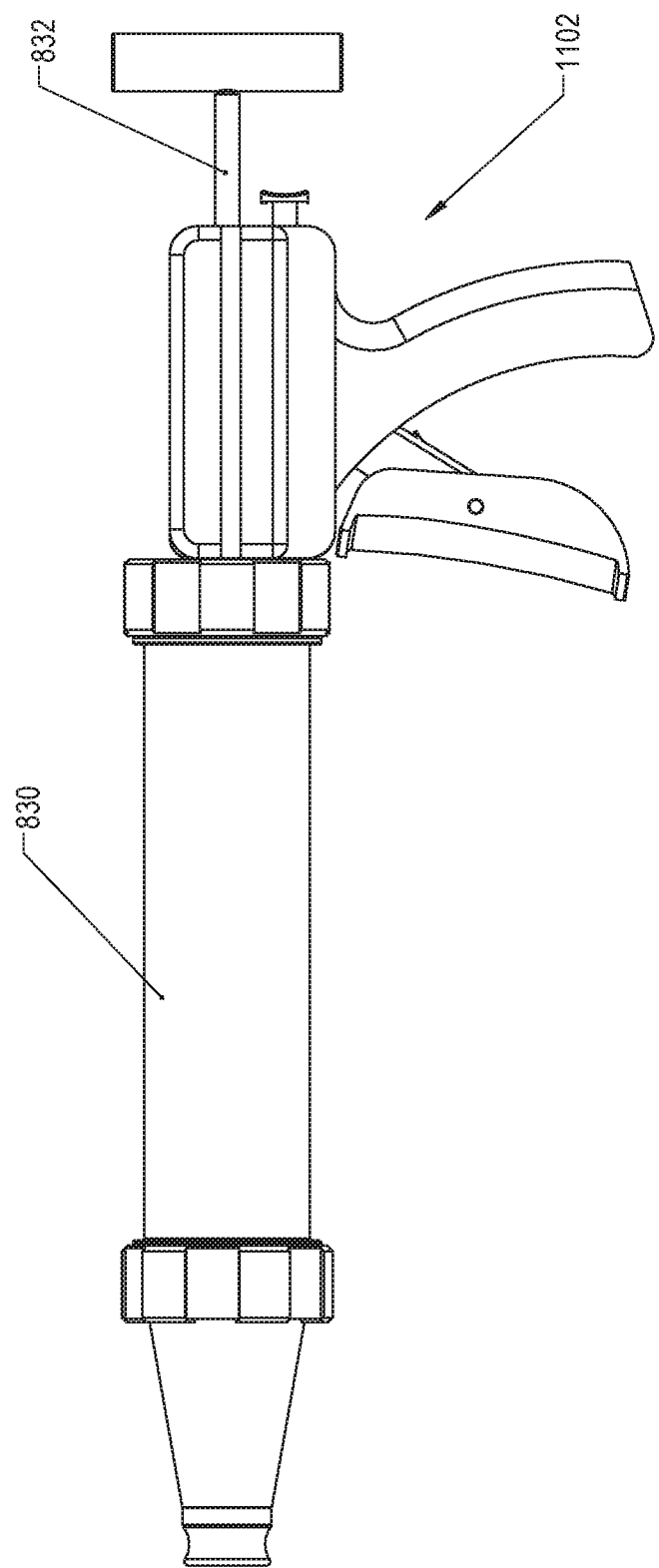
FIG. 11 shows an example of a trigger-actuated plunger gun.

FIG. 9 shows another example of the chamber 830 and plunger 832, which can be used alone or in combination with another device to help dispense the material 835, such as a peristaltic or other pump 1002, such as shown in FIG. 10, or a trigger-actuated plunger gun 1102, such as shown in FIG. 11. Unlike a pump with an impeller, the peristaltic pump 1002 can help reduce disturbance to the mechanical integrity of the silicone breast implant or other substance or material 835 during dispensing.

Figure 12:
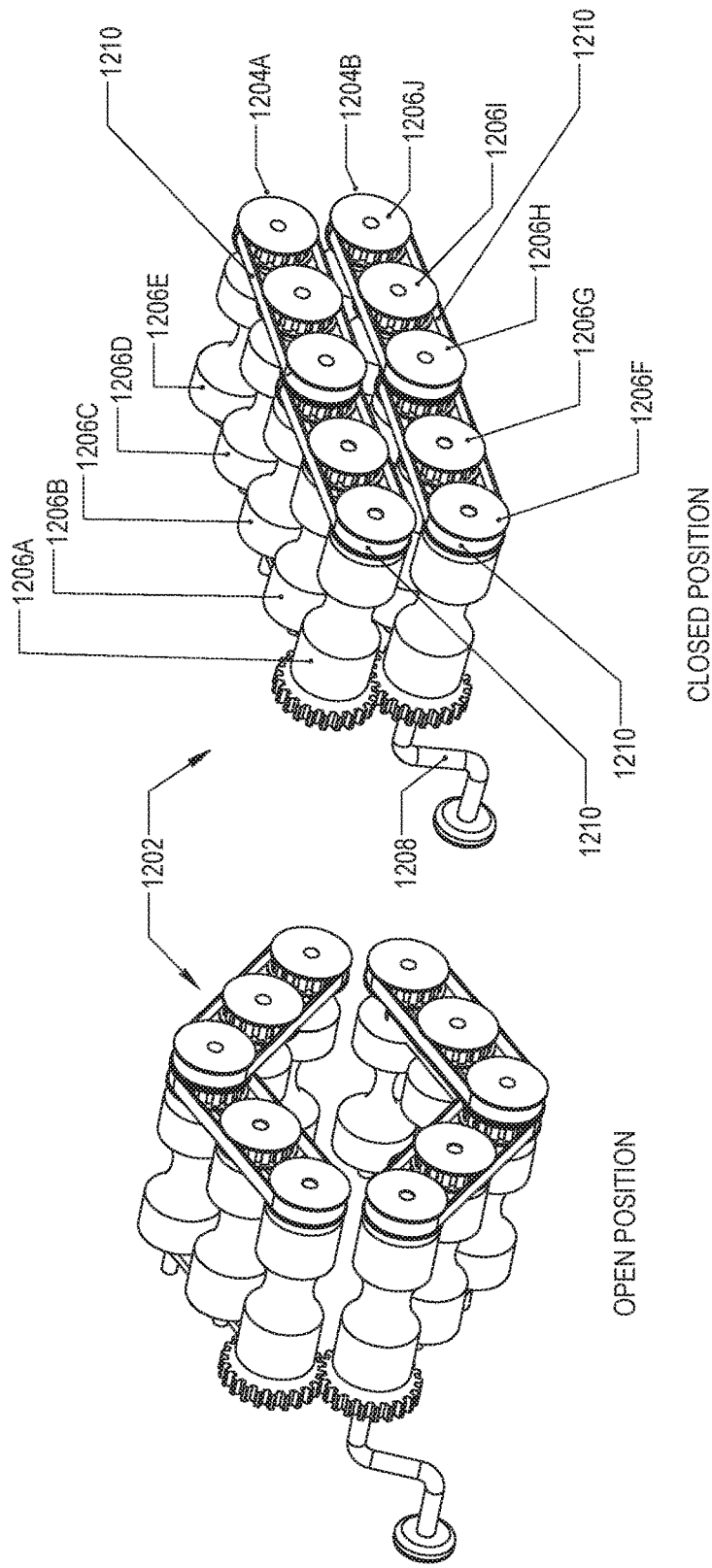
FIG. 12 shows an example of a roller pump.

FIG. 12 shows an example of a roller pump 1202 that can be integrated with one or more of the sleeve/port 414 or the ring/sleeve 412 material introducer device 825 such as to help dispense or push a silicone breast implant or other substance or material 835. Like the peristaltic pump 1002, the roller pump can help reduce disturbance to the mechanical integrity of the silicone breast implant or other substance or material 835 during dispensing. The roller pump 1202 can include top and bottom rows 1204A-B of rollers 1206. The rollers 1206 can move together in concert, such as via a crank 1208 and pulleys or belts 1210 to push the material 835, when located therebetween, in a particular direction for dispensing the material through one or more of the sleeve/port 414 or the ring/sleeve 412 material introducer device 825. Each roller 1206 can include an hourglass-like shape defining a central valley region between ends, with successive rollers 1206 having successively narrower valley regions, such as in a direction of the dispensing. One or more portions of top and bottom rows 1204A-B can optionally articulate with respect to each other, such as to allow loading of the material 835 between the top and bottom rows 1204A-B.

Various Notes

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A combination introducer and retractor medical device for introducing a device or substance through a port when the port is located at least partially within a skin incision in a human or animal subject, and for retracting skin near the incision including from underneath a layer of the skin, the medical device comprising:
   a port, providing an open channel between a proximal port opening and a distal port opening; and
   one or more blades, extending laterally perpendicularly from the distal port opening with respect to a longitudinal entry axis defined by the port, including at least one blade capable of being rotated by a user with respect to the distal port opening and also capable of being rotated by the user independently with respect to at least one other blade extending laterally perpendicularly from the distal port opening to permit separating overlying skin from underlying tissue when the port has been inserted into the incision such that the one or more blades extend laterally underneath the skin.

2. The medical device of claim 1, wherein the port includes a pair of handles extending laterally from the port from opposing sides at or near the proximal port opening.

3. The medical device of claim 2, comprising a sleeve or collar rotatable about the port, at least one of the blades extending laterally from the sleeve or collar to permit rotation together with the sleeve or collar with respect to the port.

4. The medical device of claim 3, wherein the port includes ring or other protrusion extending laterally outward from the distal port opening to capture the sleeve or collar with respect to the port and to permit captured rotation of the sleeve or collar with respect to the port.

5. The medical device of claim 4, comprising at least one of the blades extending laterally from the ring or other protrusion in a fixed manner without rotation with respect to the port.

6. The method of claim 2, wherein the sleeve or collar includes a pair of handles extending laterally from the sleeve or collar from opposing sides of the sleeve or collar.

7. The method of claim 6, wherein the pair of handles extending from the sleeve or collar is arranged to permit rotatable alignment with the pair of handles extending from the port.

8. The medical device of claim 1, wherein the one or more blades, extending laterally with respect to the port at or near the distal port opening, includes at least one blade affixed to the port and at least one blade that is rotatably mounted to the port.

9. The medical device of claim 1, wherein the port tapers inward from the proximal port opening to the distal port opening.

10. The medical device of claim 9, wherein the port is sized and shaped to permit introduction of a breast implant material through the proximal port opening and then through the distal port opening into a breast region of a human subject.

11. The medical device of claim 1, comprising a confinement chamber integrated or coupled to the port.

12. The medical device of claim 11, comprising a plunger at least a portion of which is sized, shaped, and arranged to be capable of moving with respect to the confinement chamber.

13. The medical device of claim 12, wherein the confinement chamber carries a material to be introduced into the subject assisted by the plunger.

14. The medical device of claim 1, comprising first and second portions that are rotatable with respect to each other, each portion having at least one of the blades attached thereto.

15. The medical device of claim 14, wherein the first and second portions are rotatably coupled to each other by one or more of threading, snap-fitting, tongue-and-groove, or end-flange capturing.

16. The medical device of claim 1, comprising a pump coupled to the port to provide pressurized introduction of a material into the subject via the port.

17. The medical device of claim 16, wherein the pump comprises a peristaltic pump.

18. The medical device of claim 16, wherein the pump comprises a roller pump.

19. A method of introducing a device or substance through a port into a human or animal subject via a skin incision in the subject, wherein the device includes combination introducer and retractor medical device for introducing a device or substance through a port when the port is located at least partially within a skin incision in a human or animal subject, and for retracting skin near the incision including from underneath a layer of the skin, and wherein the medical device further includes a port, providing an open channel between a proximal port opening and a distal port opening; and one or more blades, extending laterally perpendicularly from the distal port opening with respect to a longitudinal entry axis defined by the port, including at least one blade capable of being rotated by a user with respect to the port opening and also capable of being rotated by the user independently with respect to at least one other blade extending laterally perpendicularly from the distal port opening to permit separating overlying skin from underlying tissue when the port has been inserted into the incision such that the one or more blades extend laterally underneath the skin, the method comprising:
  inserting the port into the incision with the blades extending laterally perpendicularly with respect to a longitudinal entry axis defined through a distal opening of the port;
  rotating at least one blade with respect to the port and with respect to the other blade beneath a layer of skin to separate the skin from underlying tissue;
  introducing the device or substance through a proximal port opening and then through a distal port opening and into the subject via a channel provided by the port.

20. The method of claim 19, where rotating the blade includes using handles capable of being manipulated by a user using one hand to rotate the first blade with respect to the second blade.

21. The method of claim 19, comprising applying pressure to introduce material into the subject via the port.

22. The method of claim 21, wherein applying pressure includes using a pump.

23. The method of claim 21, wherein applying pressure includes using a plunger.

24. The method of claim 21, comprising using a removable cartridge or bag carrying the material.

25. The method of claim 21, wherein the material is a breast implant material.

\* \* \* \* \*